United States Patent
Hammack et al.

(10) Patent No.: US 6,679,906 B2
(45) Date of Patent: *Jan. 20, 2004

(54) CATHETER SYSTEM WITH ON-BOARD TEMPERATURE PROBE

(75) Inventors: Amy L. Hammack, San Mateo, CA (US); Jeff P. Callister, Redwood City, CA (US); Paul M. Stull, San Mateo, CA (US); Alex T. Roth, Redwood City, CA (US); William S. Tremulis, Redwood City, CA (US)

(73) Assignee: Radiant Medical, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/905,389

(22) Filed: Jul. 13, 2001

(65) Prior Publication Data

US 2003/0014094 A1 Jan. 16, 2003

(51) Int. Cl.⁷ ................................................. A61F 7/12
(52) U.S. Cl. ........................................ 607/105; 607/96
(58) Field of Search ................................ 607/105–106, 607/113

(56) References Cited

U.S. PATENT DOCUMENTS

| | | |
|---|---|---|
| 2,012,112 A | 8/1935 | States |
| 3,951,136 A | 4/1976 | Wall |
| 4,476,872 A | 10/1984 | Perlin |
| 5,211,631 A | 5/1993 | Sheaff |
| 5,271,410 A | 12/1993 | Wolzinger et al. |
| 5,486,208 A | 1/1996 | Ginsburg |
| 5,807,269 A | 9/1998 | Quinn et al. |
| 5,837,003 A | 11/1998 | Ginsburg |
| 6,019,783 A | 2/2000 | Philips et al. |
| 6,033,383 A * | 3/2000 | Ginsburg ................ 604/113 |
| 6,117,065 A * | 9/2000 | Hastings et al. ........... 600/3 |
| 6,146,411 A | 11/2000 | Noda et al. |
| 6,149,673 A * | 11/2000 | Ginsburg ................ 607/106 |
| 6,149,676 A | 11/2000 | Ginsburg |
| 6,224,624 B1 | 5/2001 | Lasheras et al. |
| 6,231,594 B1 * | 5/2001 | Dae ...................... 607/106 |
| 6,264,679 B1 * | 7/2001 | Keller et al. ............ 606/21 |
| 6,290,717 B1 * | 9/2001 | Philips ..................... 600/20 |
| 6,299,599 B1 * | 10/2001 | Pham et al. ........ 604/101.03 |
| 6,366,818 B1 * | 4/2002 | Bolmsjo ................. 607/101 |
| 6,368,304 B1 | 4/2002 | Aliberto et al. |
| 6,371,979 B1 * | 4/2002 | Beyar et al. ............. 606/108 |
| 6,383,144 B1 * | 5/2002 | Mooney et al. ........... 600/435 |
| 6,419,643 B1 | 7/2002 | Shimada et al. |
| 6,447,474 B1 | 9/2002 | Balding |
| 6,497,721 B2 | 12/2002 | Ginsburg et al. |

FOREIGN PATENT DOCUMENTS

FR WO 94/01177 * 1/1994 ............ A61N/5/02

* cited by examiner

Primary Examiner—Roy D. Gibson
Assistant Examiner—Henry M. Johnson
(74) Attorney, Agent, or Firm—Robert D. Buyan; Stout, Uxa, Buyan and Mullins, LLP

(57) ABSTRACT

A catheter system for controlling the body temperature of a patient by modifying the temperature of blood flowing within a blood vessel of the patient. The catheter system comprises a catheter body having a heat exchange region in contact with the blood; and a temperature probe having a distal end that extends from the catheter body, thereby monitoring the temperature of blood flowing within the blood vessel.

38 Claims, 11 Drawing Sheets

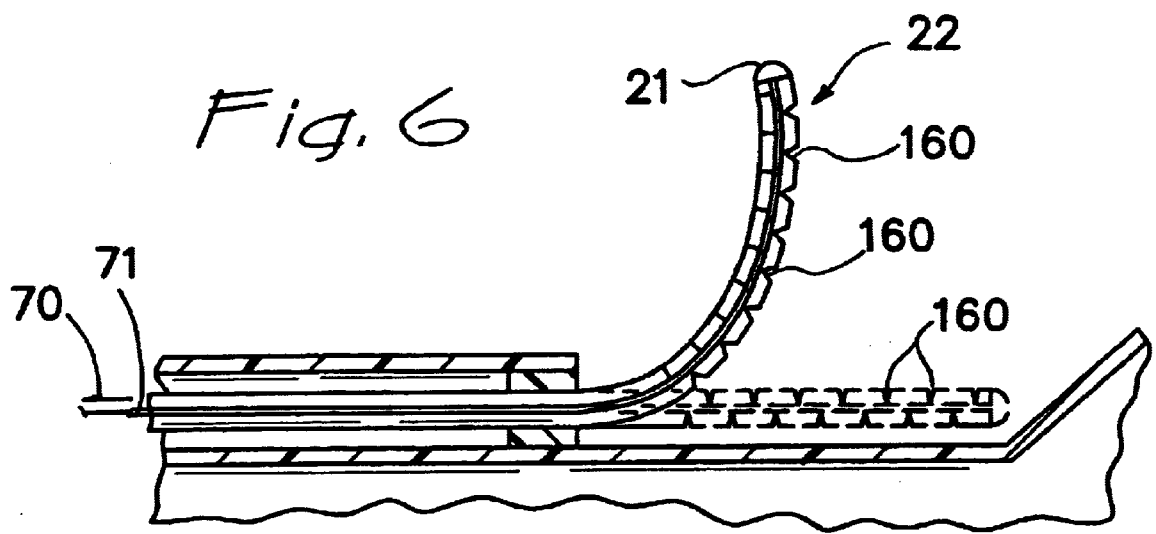
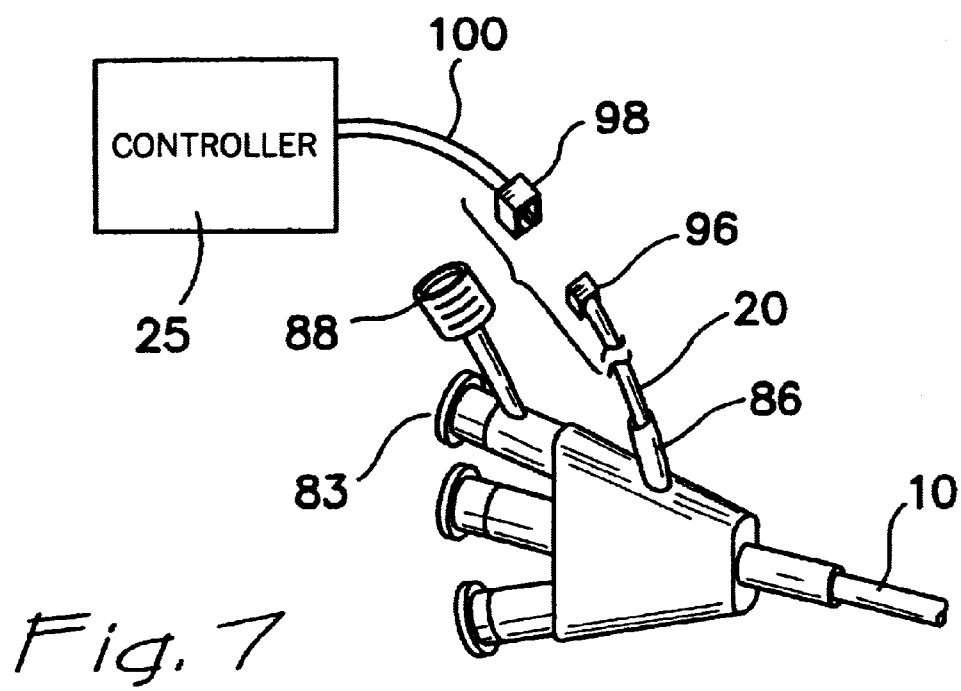

CATHETER SYSTEM WITH ON-BOARD TEMPERATURE PROBE

BACKGROUND OF THE INVENTION

1. Field of the Invention

The present invention relates generally to medical devices and a method of using them for selectively affecting the temperature of a patient's body, or a portion of the patient's body, and more particularly, to a temperature control catheter system including an on-board temperature probe and a method of use thereof.

2. Description of the Prior Art

Under ordinary circumstances, the thermoregulatory system of the human body maintains a near constant temperature of about 37° C. (98.6° F.), a temperature generally referred to as normothermia. For various reasons, however, a person may develop a body temperature that is below normothermia, a condition known as hypothermia, or a temperature that is above normothermia, a condition known as hyperthermia. Accidental hypothermia and hyperthermia are generally harmful, and if severe, the patient is generally treated to reverse the condition and return the patient to normothermia. Accidental hypothermia significant enough to require treatment may occur in patients exposed to overwhelming cold stress in the environment or whose thermoregulatory ability has been lessened due to injury, illness or anesthesia. For example, this type of hypothermia sometimes occurs in patients suffering from trauma or as a complication in patients undergoing surgery.

However, in certain other situations hyperthermia and particularly hypothermia may be desirable and may even be intentionally induced. For example, hypothermia is generally recognized as being neuroprotective, and may, therefore, be induced in conjunction with cardiac surgery where there is an interruption or decrease of cardiac output of oxygenated blood, treatments for ischemic or hemorrhagic stroke, blood deprivation caused by cardiac arrest, intracerebral or intracranial hemorrhage, head and spinal trauma, brain or spinal surgery, or any other situation where there is danger to neural tissue because of ischemia, increased intracranial pressure, edema or other similar processes.

Other examples where hypothermia may be neuroprotective include periods of cardiac arrest in myocardial infarction and heart surgery, neurosurgical procedures such as aneurysm repair surgeries, endovascular aneurysm repair procedures, spinal surgeries, procedures where the patient is at risk for brain, cardiac or spinal ischemia such as beating heart by-pass surgery or any surgery where the blood supply to the heart, brain or spinal cord may be temporarily interrupted.

Hypothermia has also been found to be protective of cardiac muscle tissue when that muscle tissue is at risk, for example during or after a myocardial infarct (MI), or during cardiac surgery, cardiac arrest, or other situations where there is deprivation of the normal blood supply to the cardiac tissue. Indeed the tissue protective nature of hypothermia in general is recognized in a vast array of situations.

Simple surface methods for cooling such as cooling blankets, immersion in cold water or ice baths, or alcohol rubs are generally ineffective for inducing hypothermia. The body's normal thermoregulatory responses such as vasoconstriction of capillary beds at the surface of the body and arterio-venous shunting of blood away from the skin act to render such cooling methods ineffective. Further, if the body temperature drops sufficiently below normothermia, usually at about 35.5° C., the body begins to shiver as a thermoregulatory response to generate additional metabolic heat and fight the induction of hypothermia. This may increase the generation of metabolic heat by 200–500% and generally makes induction of hypothermia in an awake patient impossible by surface cooling alone. Further, the shivering itself is so uncomfortable and exhausting for the patient that this is altogether unacceptable for an awake patient. Only if the patient is paralyzed, which necessitates the patient be intubated for breathing and be placed under general anesthesia can the patient be subjected to significant surface cooling. Even under these conditions, surface cooling which necessitates cooling through the skin and surface fat layers and the use of generally low power surface cooling devices, is too slow and inefficient to be an acceptable means of inducing therapeutic hypothermia.

Furthermore, if control of the patient's temperature is desired so as to attain and maintain a target temperature (sometimes but not always normothermia), or to reverse hypothermia and re-warm the patient at a predetermined rate, surface cooling and warming far too slow and inefficient to give the required level of prompt and precise change in the patient's core temperature to allow these methods to control the patient's thermal condition.

A patient's temperature may be controlled by a very invasive method of adding heat to or removing heat from a patient's blood, particularly in the case of heart surgery. Blood is removed from a patient, circulated through a heart-lung by-pass system, and reintroduced into the patient's body. The equipment generally has a temperature control unit that heats or cools the blood as it is circulated out of the patient before it is reintroduced into the patient. Because a large volume of blood is circulated through the machine in a short time, this by-pass method may be both fast and effective in changing the patient's core temperature and in controlling that temperature, but has the disadvantages of requiring a very invasive medical procedure which requires the use of complex equipment, a team of highly skilled operators, is generally only available in a surgical setting where the patient has undergone a thoracotomy (had its chest split and opened), and involves mechanical pumping of a huge quantity of the patient's blood and channeling that blood through various external lines and conduits, all of which is generally very destructive of the blood tissue resulting in the cytotoxic and thrombolytic problems. In fact, most surgeons using such by pass machinery tend to avoid its use for longer than four hours, much less if at all possible, which is an inadequate period of time for treatment of some conditions such as stroke.

One method for adding or removing heat from a patient by adding or removing heat from the patient's blood that does not involve pumping the blood with an external, mechanical pump is by placing a heat exchange catheter in the bloodstream of a patient and exchanging heat through the catheter. This endovascular temperature management (ETM) technique was described in U.S. Pat. No. 5,486,208 to Ginsburg, the complete disclosure of which is incorporated herein by reference. The Ginsburg patent discloses a method of controlling the temperature of a body by adding or removing heat to the blood by inserting a heat exchange catheter having a heat exchange region into the vascular system and exchanging heat between the heat exchange region and the blood to affect the temperature of a patient. One method disclosed for doing so includes inserting a catheter having a heat exchange region comprising a balloon into the vasculature of a patient and circulating warm or cold heat exchange fluid through the balloon while the balloon is in contact with the blood.

In successful ETM, in addition to fast and precise changes in a patient's body temperature, fast and precise control over a patient's thermal condition is very important whether the patient is being cooled, warmed, or maintained at a constant temperature. A general apparatus and method of ETM control based on temperature management responsive to feedback from temperature probes in or on the patient is disclosed in U.S. Pat. No. 6,149,673 to Ginsburg, the complete disclosure of which is incorporated herein by reference. A similar method is described in PCT publication WO 01/10494 to Radiant Medical Inc., the complete disclosure of which is also incorporated herein by reference. In such methods, a signal representing the temperature of a target tissue, which as mentioned may be the core body temperature, is directed to a controller from a temperature probe inserted on or in the patient, and the controller then controls the exchange of heat between the heat exchange catheter and the patient's blood flowing past that catheter. That in turn controls the temperature of the patient. With such a method, it is clear that precise, accurate and convenient control is dependent to a large extent on the precise, accurate, and convenient temperature measurement of the temperature of the target tissue (which may be the core body temperature) and thus dependent on a precise, accurate and convenient temperature probe.

Currently, the patient's temperature may be measured by any one or several generally available temperature probes. These include, for example, skin temperature probes, tympanic probes that may be placed in the ear canal and perhaps even in physical contact with the ear drum, esophageal probes including nasoesophageal probes, rectal probes, bladder probes, temperature sensors placed on an insertion sheath, and temperature probes that may be inserted by needle directly into the target tissue. Each of these techniques, however, suffers from significant shortcomings.

Some probes may not give an accurate temperature of the target tissue and therefore may not provide the information necessary for controlling the ETM procedure. For example, if the target is the core temperature of the patient, a skin temperature is generally not an accurate representation of the core temperature; if cardiac muscle is the target tissue, a bladder probe might not be sufficiently accurate. The probe might not be sufficiently responsive to changes in temperature to provide a current temperature of the target temperature. For example, a rectal temperature probe is generally very slow to respond to temperature changes in the core, and thus if the controller is receiving its temperature signal from a rectal probe, it might not be able to respond with sufficient speed and precision to changes in the core temperature. Bladder temperature probes also tend to suffer from this problem. Some probes are awkward and too difficult to use. For example, tympanic probes are difficult to place and tend to fall out and thus not provide an accurate temperature measure. Where a temperature probe is controlling an ETM procedure and thus in the patient at the same time as an ETM catheter, it may reflect the temperature of the ETM catheter rather than the target tissue if the probe is located too close to the catheter. Probes placed on the insertion sheath, for example, may tend to be unduly influenced by the heat exchange catheter placed through the sheath. Other probes may measure the temperature of the target tissue, but have other disadvantages that make their use undesirable. For example, needle temperature probes that are stuck directly into the target tissue, of course, measure the temperature of the target tissue, but are invasive and require the patient suffer an additional needle stick. They are also dependent on accurate placement in the first instance which may be a difficult and highly skilled procedure, and require that they do not move after placement, requiring constant monitoring and taping or the like which may be obtrusive and awkward.

If redundancy is important for safety, as it usually is in a controlled ETM procedure, all of the above devices would generally require the placement of two probes. This may require two probes placed in different locations that may reflect different temperature profiles, a very real problem for controlling ETM. It may require that two probes be attached together, which makes the probes large and often clumsy to use.

Very importantly, when used to control an ETM procedure, all of the above require a device (the probe) in addition to the ETM catheter already being inserted into the patient's body. These are generally separately placed requiring an additional procedural step, are often quite distal to the insertion site of the catheter but must still be attached to the controller that is attached to the ETM catheter. This may greatly complicate what may already be a crowded operating room or other area and add undesirable complexity to the procedure.

For ETM to accurately control the temperature of a target tissue, it is important that the temperature measured by the probe provides current and accurate measurement of the temperature of the target tissue and responds quickly to changes in temperature of the target temperature. This is not always the case with the probes mentioned above. If the controller precisely and rapidly responds to the temperature feedback to control the temperature of the target tissue, for example if the patient's temperature is being increased at a very precise rate of, for example, 0.2 C. per hour, the controller must act to add heat when the temperature is not increasing fast enough, remove heat if the body is adding metabolic heat so fast that it would result in rewarming too fast, or maintain the temperature of the heat exchange catheter the same as the blood if the patient's temperature is increasing at exactly the correct rate. The systems described in the publications incorporated above may be capable of such precision, but rely on temperature information from the temperature probes that is current and accurate.

Temperature probes placed directly in the bloodstream in one of the great vessels such as the inferior vena cava (IVC) generally accurately reflect the core body temperature which is also generally the temperature of the brain or heart tissue, currently the two most common target tissues for ETM, but if the probe is placed some distance from the heat exchange catheter such placement usually involves an additional incision or puncture into the vasculature, and if the probe is placed in the same general vicinity as the heat exchange catheter, there is a likelihood that the temperature reading will be unacceptably influenced by the heat exchange region on the catheter or the temperature of the catheter shaft and thus not represent the temperature of the target tissue sufficiently to serve as a control temperature for the system.

Further, when the temperature probe is placed in the vasculature in general, the distal tip of the probe which generally houses the temperature sensor itself may come into contact with the wall of the vessel. In such a case, the temperature that is sensed will be that of the vessel wall and not of the blood. While these two temperatures may often be the same, there will be occasions where they may be unacceptably different. Furthermore, the distal tip of such a probe must be designed so that it will not be traumatic to the vessel wall. It would be best, of course, if contact with the vessel wall could be avoided altogether.

When any device is inserted into a patient, the physician generally would prefer to make as small an incision or puncture as possible. Thus where a probe is inserted into the bloodstream, a low profile is generally preferable. If the probe is attached or otherwise associated with another device that is being inserted into a patient, a means to keep the overall profile to the device being inserted would be desirable.

Accordingly, it would be helpful to have a temperature probe that was easy to place in conjunction with an ETM procedure.

It would also be helpful to have a temperature probe that precisely and accurately measured a relevant tissue temperature for ETM.

It would also be helpful to have a temperature probe that rapidly responded to changes in temperature in a target tissue.

It would also be helpful to have a temperature probe that did not create additional crowd the treatment area during treatment by ETM.

It would also be helpful to have a temperature probe that did not require additional punctures or incisions in a patient undergoing ETM.

It would also be helpful to have a temperature probe that had a deployed and an undeployed configuration.

Accordingly, it would be helpful to have a temperature probe located in the blood stream at a location close to the heat exchange catheter to accurately measure the temperature of the blood but not be unduly influenced by the temperature of the heat exchange catheter.

It would be helpful to have a temperature probe that had a plurality of temperature sensors for redundancy and safety.

It would be helpful to have a temperature probe that had an atraumatic distal tip.

It would be helpful to have a temperature probe that could be advantageously inserted into the vasculature of a patient undergoing ETM without the need of a second incision or puncture.

It would be helpful to have a temperature probe that was an on-board temperature probe.

It would be helpful to have a temperature probe that had a deployed and an undeployed position, wherein the operator could move the probe between the deployed and the undeployed configuration.

Furthermore, it would be helpful to have a system and method that ensure that the temperature reading provided at the heat exchange catheter is accurate in order to ensure appropriate operation of the heat exchange catheter.

SUMMARY OF THE INVENTION

The present invention provides a catheter that includes an on-board temperature sensor.

In one aspect of the invention, the present invention provides a catheter system for sensing the temperature of a patient. The catheter system includes a catheter having a shaft, a heat exchange region and a temperature probe lumen. The temperature probe lumen defines an aperture that is located proximal of the heat exchange region. A deployable temperature probe is provided that includes a temperature sensor and a signal carrying mechanism that extends from the sensor to a location outside of the patient. The temperature probe has an undeployed configuration and a deployed configuration and is movable between the undeployed and deployed configurations. When the temperature probe is in the deployed configuration, the temperature sensor is located further from the shaft than when the temperature probe is in the undeployed configuration. The temperature sensor generates a signal representing a sensed temperature and the signal carrying mechanism transmits the signal from the temperature sensor to the location outside the patient.

In accordance with one aspect of the present invention, the distal end of the movable temperature probe comprises a thermistor.

In accordance with a further aspect of the present invention, the distal end of the temperature control lumen includes a ramp coupled to the opening.

In accordance with yet another aspect of the present invention, the opening is in the form of a flat slot and a portion of the temperature probe is flat.

In accordance with yet another aspect of the present invention, the movable temperature probe includes an atraumatic tip at the distal end portion.

In accordance with yet another aspect of the present invention, the movable temperature probe comprises a shape memory metal such as nickel-titanium alloy (nitinol) at a tip portion of the distal end portion.

The present invention also provides a temperature probe that includes two temperature sensors.

The present invention also provides a temperature probe having a heat memory shaped distal portion containing a temperature sensor wherein the distal portion of the probe assumes a shape when warmed by blood flow that positions the temperature sensor away from the catheter shaft;

The present invention also provides a catheter shaft having channels for the flow of heat exchange fluid and a temperature sensor that is positioned by the inflation of a balloon on the catheter shaft at a location away from the heat exchange fluid channels;

The present invention also provides a catheter system having a temperature probe with a temperature sensor in its distal portion, the temperature sensor is deployable to locate the temperature sensor away from the catheter shaft;

The present invention also provides a catheter system with a temperature sensor that has a first configuration having one profile for insertion, and a second configuration that has a greater profile wherein the temperature sensor is located farther away from the catheter shaft in the second configuration than in the first configuration;

The present invention also provides a method of monitoring the body temperature of a patient by monitoring the temperature of blood flowing within a blood vessel of the patient. The method includes advancing a catheter body comprising a temperature control lumen coupled to the catheter shaft wherein the temperature control lumen includes an opening defined at a distal end of the catheter, into the patient's blood vessel such that the opening is in contact with the patient's blood. The method further includes moving a temperature probe within the temperature control lumen such that a distal end portion of the movable temperature probe protrudes through the opening into the blood flowing within the blood vessel.

The present invention thus provides catheters and methods for inducing or treating hypothermia or hyperthermia by inserting a catheter body into a blood vessel of the patient, moving a temperature probe into the blood stream within the blood vessel and selectively transferring heat either to or from the blood flowing through the vessel while monitoring the temperature of the blood stream. It enhances the ability to monitor the temperature of the blood stream, thereby enhancing both the ability to induce or treat hypothermia or hyperthermia and the ability to rapidly and precisely control the body temperature of the patient.

Other features and advantages of the present invention will be understood upon reading and understanding the detailed description of preferred exemplary embodiments found herein below, in conjunction with reference to the drawings, in which like numerals represent like elements.

BRIEF DESCRIPTION OF THE DRAWINGS

FIG. 6 is a sectional side view of a distal end portion of a temperature probe lumen in accordance with an alternative embodiment of the present invention.

FIG. 7 is an elevational view of the cable and connector of the invention;

DESCRIPTION OF SPECIFIC EXEMPLARY EMBODIMENTS

Figure 1:
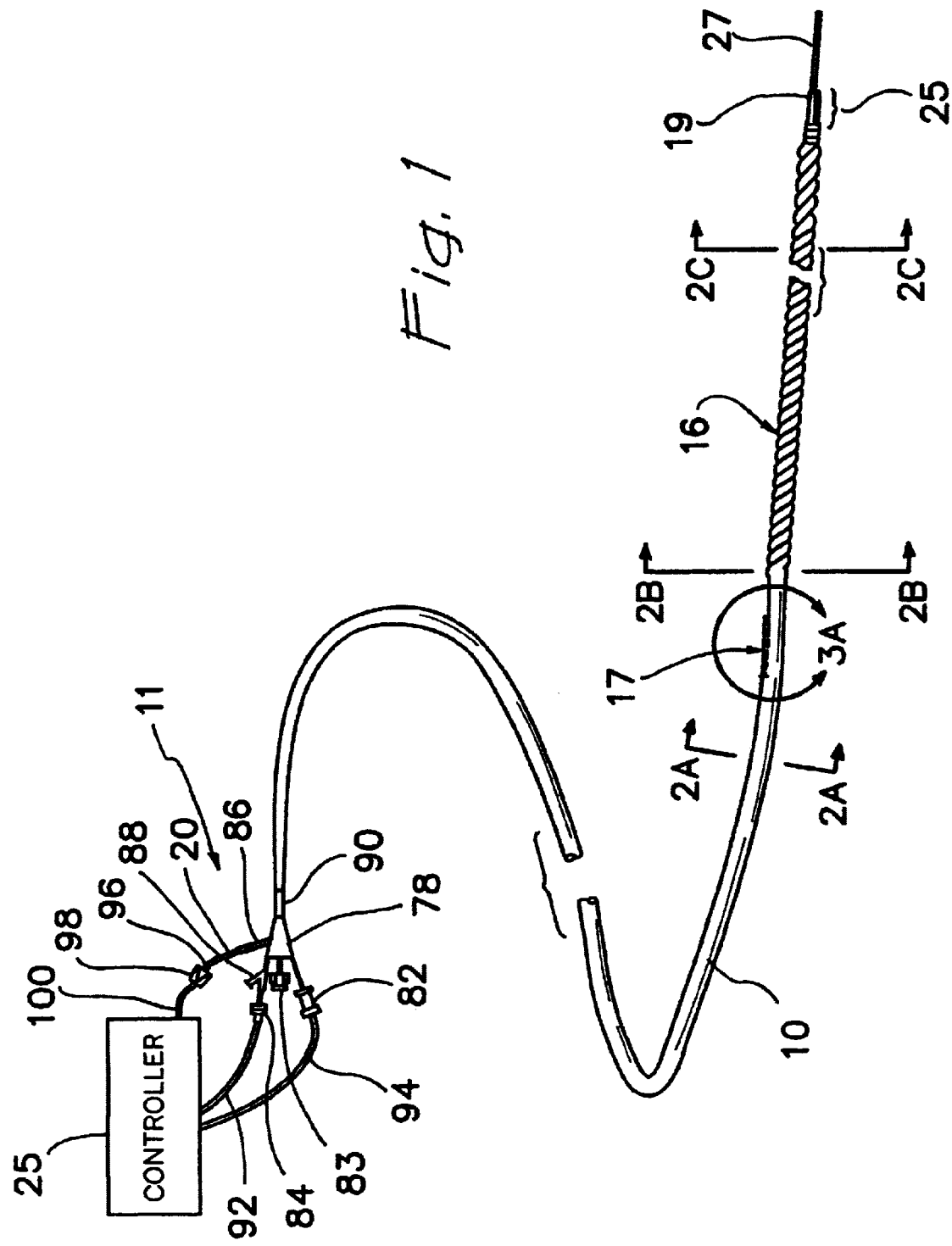
FIG. 1 is a perspective view of a catheter system in accordance with the present invention.

Referring to FIG. 1, a heat exchange catheter system that includes a catheter body 10 is illustrated. Catheter body 10 may comprise any type of heat exchange catheter. Numerous suitable examples of heat exchange catheter systems which may comprise the present catheter body 10 are found in various U.S. Patents, and the present invention may be adapted for use with a wide variety of such different temperature regulating catheter systems. For example, in accordance with the present invention, the catheter system used may comprise a catheter system adapted for warming the body fluid passing thereover (for example, a system having an electric heater disposed therein, or a catheter with a heat exchange region thereon which is warmed by circulating warm heat exchange fluid therethrough). In addition, the catheter system used may comprise a catheter system adapted for cooling the body fluid passing thereover (for example, a catheter with a heat exchange region such as a heat exchange balloon or the like thereon, which heat exchange region is placed in the blood stream and cooled by pumping a cooled fluid flow therethrough). Furthermore, those skilled in the art will understand that even non-heat exchange catheters may be used with the present invention if a catheter having an on-board deployable temperature probe is desirable.

Figure 3A:
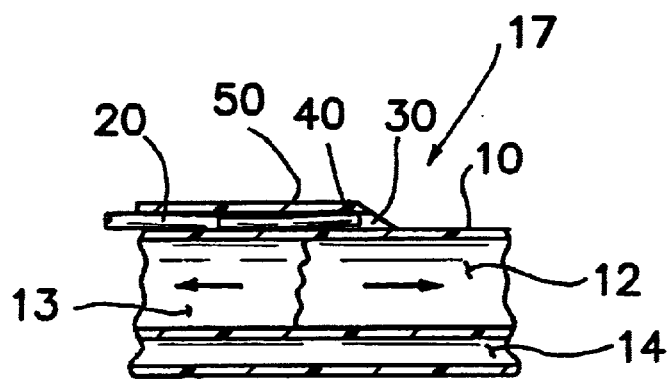
FIG. 3A is a sectional view of the catheter illustrated in FIG. 1 of the portion of the catheter of FIG. 1 contained in circle 3A—3A.

In the embodiment of the invention illustrated in FIG. 1, catheter body or shaft 10 includes a proximal end portion 11 in the form of a Y adaptor, a heat exchange region 16 on the distal portion of the catheter in the form of a helically wound multi-lobed balloon, a temperature probe exit region 17 as illustrated in FIG. 3A, and a distal end 19 having a soft, atraumatic tip 25.

Figure 2A:
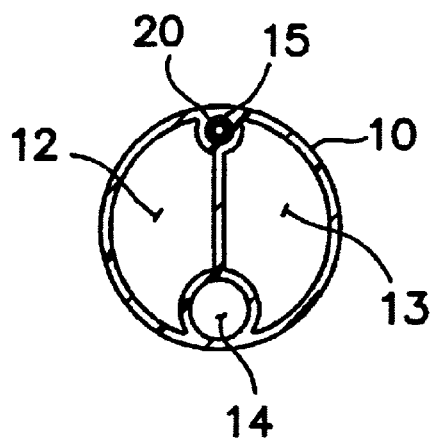
FIG. 2A is a sectional view of the catheter illustrated in FIG. 1 taken along the line 2A—2A.
Figure 2C:
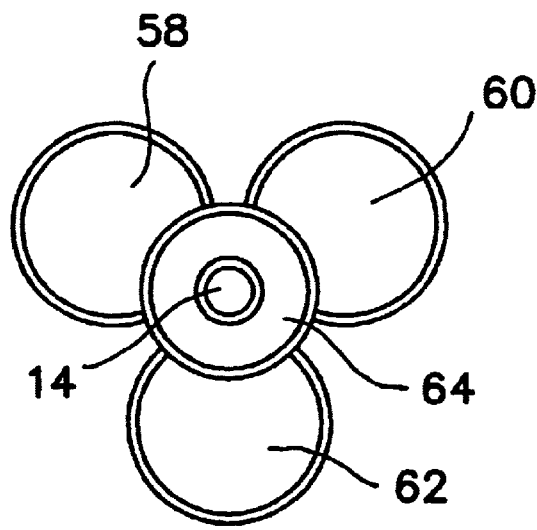
FIG. 2C is a cross section of the balloon portion of the catheter taken along the lines 2C—2C in FIG. 1.

The heat exchange region 16 is heated or cooled by the flow of a heat exchange liquid therethrough. Referring to FIG. 2A, the shaft 10 has four lumens therein proximal of the temperature probe exit region 17, and three lumens therein immediately distal of that region. Proximal of that region, the shaft includes an inflow lumen 12, an outflow lumen 13, a guidewire lumen 14 and a temperature probe lumen 15. The transition between the four lumen (FIG. 2A) and three lumen (FIG. 2B) catheter tubing may be made by merely skiving off the top portion of the tube, or may result from joining a three lumen extrusion to a four lumen extrusion using extension tubes between the three lumens that remain in the distal shaft and placing an external jacket around that joined length of catheter shaft made of the two different extrusions. The jacket may be heat shrunk or heat welded around the tubes to secure the joint. Outflow lumen 13 is fluidly connected between outflow connector 84 and outflow lumens 58, 60, 62. Inflow lumen is fluidly connected between inflow connector 82 and balloon inflow lumen 64. A complete description of heat transfer catheters similar to that described here is included in U.S. Pat. No. 6,231,594 B1 owned by applicant's assignee and incorporated herein in full, and U.S. application Ser. No. 09/777,612.

The proximal end of the catheter of the invention terminates in a Y adaptor 78 which is attached to an outflow connector 84, an inflow connector 82, a guide wire lumen terminus 83, a temperature probe lumen terminus 86, and an aspiration valve 88. A short length of strain relief tubing 90 may be placed over the catheter at the location where it attaches to the Y adaptor. The outflow connector may fluidly connect the outflow lumen 13 to an outflow line 92 carrying heat exchange fluid between the outflow lumen and the controller 25. The inflow connector fluidly connects the inflow lumen of the catheter 12 to an inflow line 94 that carries heat exchange fluid from the controller to the inflow lumen. The inflow connector 82 may be closed, and the heat exchange fluid in the balloon withdrawn through the aspiration valve 88 when it is desired to collapse the balloon, for example when the catheter is to be withdrawn from within the vasculature of a patient. The guide wire lumen terminus provides access from the Y adaptor to the guide wire lumen 14 that extends entirely through the catheter for insertion of a guide wire 27 therethrough. The guidewire lumen also functions as a working lumen for the injection of drugs, thrombolytics, or other substances from outside the body to a location distal to the catheter, or for sensing the pressure of the blood stream distal of the catheter. It is also possible to insert other devices through the lumen, for example a temperature sensor for sensing the temperature distal of the heat exchange balloon, an angioplasty catheter for treating the patient at a location distal of the balloon, an angiojet type device or any similar type device for treatment distal of the balloon. In fact, it is possible if a temperature is sensed proximal of the balloon, and another temperature is sensed distal of the balloon, and the amount of energy emitted or absorbed by the balloon is determined, to determine blood flow.

The proximal portion of the temperature probe 20 exits the catheter from the temperature probe lumen terminus 86. The proximal end terminates in an appropriate plug, for example a plastic clip type plug 96. That plug, in turn, attaches to a clip type jack 98 reminiscent of the type of plastic clip attachments common in telephones and similar devices. This plug to jack attachment connects the temperature probe electrically to the temperature probe cable 100 which in turn is connected to the controller. This provides for temperature signals generated by the temperature probe as will be described below to be transmitted to the controller so that the controller may control the heating and cooling effected by the catheter based on temperature feed back from the patient as described in U.S. Pat. Nos. 6,149,673 and 6,149,676 incorporated herein in full. The controller may control the exchange of heat between the blood and the heat exchange region by altering the temperature of the heat exchange fluid or by altering the flow rate of the heat exchange fluid through the catheter, or some combination thereof, in response to the temperature signal. One controller suitable for receiving temperature signals generated by the present invention and using said signals to control the transfer of heat from a patient is described in U.S. patent application Ser. No. 09/707,257 incorporated herein in full.

A temperature probe 20 is included and is movable within temperature probe lumen 15. As can be seen in FIGS. 3b, 4, 5 and 6, the temperature probe preferably includes temperature sensor such as a thermistor 21 at its distal end portion 22. Other temperature sensors may be employed, for example a thermocouple, light probes capable of sensing temperature, infra red sensors, or similar devices, as long as the sensor is able to sense the temperature of a specified tissue and generate a signal representing that temperature that may subsequently be transmitted to a controller for controlling the heat exchange of a heat exchange catheter or for some other desired purpose. In the example as shown in this embodiment, the temperature sensor is a thermistor, the temperature sensed is that of the blood surrounding the thermistor, and the signal generated is an electrical signal representing that temperature. Thermistors have been found to be advantageous because they can be made very small and because they can be made sufficiently accurate.

At least a portion 23 of the temperature probe adjacent its distal end portion generally comprises insulating materials. A coating of plastic 106, as in encasing the signal wires 102, 104 within a plastic tube, may be sufficient. It is important that the wires that carry the electric signal from the thermistor be sufficiently insulated that they do not conduct the temperature of the heat exchange catheter to the thermistor and thereby significantly influence the temperature sensed by the thermistor.

For safety reasons, it is generally preferable that there be redundancy in the temperature sensors. For example, the distal portion of the temperature probe may contain two thermistors each of which has independent connector wires that extend down the probe to the connection 96/98 and thus to the controller. The controller is generally programmed so that if the two signals do not correspond to each other within some predetermined range, the controller responds appropriately. For example, it may sound an alarm; it may flash a warning on a user interface if it has one; it may cease to provide hot or cold heat exchange fluid to the catheter, or any combination including all of the above. While this redundancy will generally not be repeated as to each embodiment described below, it is to be understood that such redundancy may be a feature incorporated into each embodiment. Furthermore, the redundancy may be accomplished by incorporating two or more sensors in each probe, or by incorporating more than one embodiment of the probe in a particular catheter.

Figure 2B:
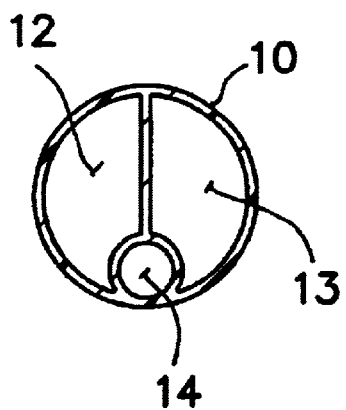
FIG. 2B is a sectional view of the catheter illustrated in FIG. 1 taken along the line 2B—2B.

FIGS. 2A, 2B illustrate cross sections of the catheter depicting the portion of the catheter shaft containing the temperature probe lumen. The inner diameter of temperature probe lumen 15 is generally in a range of 0.020" to 0.035". Preferably, the inner-diameter of the temperature probe lumen is about 0.030 and may not be round, depending on the extrusion. The temperature probe along its length is configured to move through the lumen, for example, the probe may comprise a tube with thermistors in it near the distal end and wires for transmitting a signal from the thermistors contained within the tube. The tube may have, for example an outer diameter of about 0.025 or less. As described below, the diameter of the probe along its length may vary. For example, a portion may be flat for alignment with a flat exit ramp; a portion may have a slightly larger diameter so that it cannot be entirely withdrawn, or the like. If the probe is of the type that is moved within the temperature probe lumen, the probe, the lumen, or both may be constructed of material that slides easily against the other such as PTFE (Teflon™) or FEP.

Figure 4:
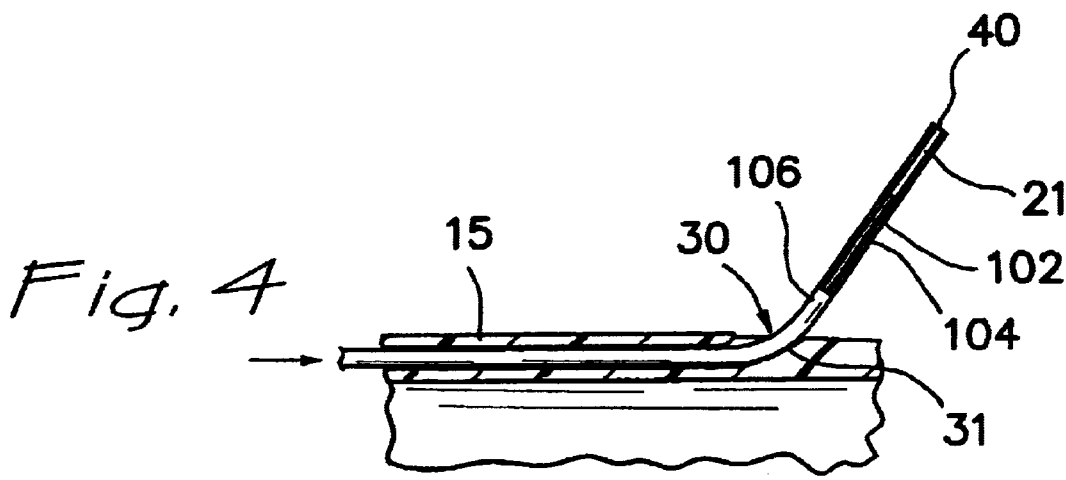
FIG. 4 is a sectional side view of a distal end portion of a temperature probe lumen in accordance with an alternative embodiment of the present invention.

FIG. 4 illustrates a slot 30 at the distal end portion of the temperature control lumen. The slot is provided to allow thermistor 21 of temperature probe 20 to protrude from the catheter in order that the thermistor may be advanced away from the catheter shaft and into the blood stream when the catheter is inserted into a subject's blood vessel. As can be seen in FIG. 4, the thermistor preferably curls into a substantially J-shape so that it moves away from the catheter and any effects of the temperature generated by the heat exchange catheter, thus allowing the thermistor to obtain a more accurate measurement of the temperature of blood flow of the subject. Preferably, the tip of the temperature probe containing the thermistor moves at least 1.8 mm away from the catheter. The temperature control catheter generally contains a flow of heat exchange fluid at a temperature different than the blood temperature of the patient, and it has been found that if a temperature is sensed by the thermistor at a distance greater then 1.8 mm from the shaft of the catheter, it generally accurately represents the temperature of the blood flowing within the vessel and is not unduly influenced by the temperature of the catheter shaft. It may be possible to advance the probe too far, however. For example, if the catheter is in a vessel and the sensor is too far away from the shaft, the sensor may impact on the vessel wall. Likewise, if the sensor portion of the temperature probe is extended too far out of the temperature probe lumen, it may prolapse back onto the catheter shaft and the temperature sensed may be significantly influenced by the temperature of the catheter shaft.

The location of the distal exit opening in the temperature probe lumen along the length of the catheter is also important. When the catheter is used for whole body cooling in the inferior vena cava (IVC) the catheter is generally inserted through an introducer sheath into the femoral vein and advanced so that the balloon is located entirely in the IVC. So that the cooling may be maximized, it is desirable that the balloon occupy as much as possible of the IVC. That means that the shaft of the catheter is located to a large extent in the femoral vein, a much smaller vein than the IVC. In fact the shaft extends all the way back through the introducer sheath. The blood in the introducer sheath tends to flow very little if at all, and therefore to be greatly influenced by the temperature of the catheter shaft. Thus it is desirable that the temperature sensed be that of the blood in the IVC and not in the femoral vein or in the introducer sheath. Yet if the sensor is too close to the balloon, the effective heat exchange region, it is likely to be greatly influenced by the temperature of the heat exchange fluid. Therefore the exit of the temperature probe lumen is desirably as close to the balloon as possible to ensure that it is measuring the temperature of the blood in the IVC and not the femoral vein, or the introducer sheath, and yet far enough away from the balloon to accurately sense the temperature of the blood and not be unduly influenced by the temperature of the heat exchange fluid in the balloon. It has been found that if the probe lumen exit slot 30 is located about 0.5 cm or more proximal of the heat exchange region, this is generally acceptable. (The closeness of the probe tip to the expanded balloon also has the important advantage of allowing the balloon to somewhat act as a bumper to shield the tip of the probe from contacting the wall of the vessel.)

Likewise, the length that the probe extends from the exit opening in the lumen is important. Besides not prolapsing on the catheter shaft, it is important that the probe not extend far enough to lay against the balloon. Again, in this embodiment, it has been found that generally a gentle J shaped extension resulting in the thermistors being extended at least 1.8 mm from the shaft is desirable.

As can be seen in FIG. 4, the end of the temperature probe lumen preferably includes a ramp 31 leading up to the opening. Thus, when the thermistor portion of the temperature control probe encounters the ramp, the ramp directs the thermistor up and through slot 30 into the blood stream. The end of the probe is generally shaped in a gentle J shape in a manner well know to those in the art of guide wires and like probes, and is constrained in a relatively straight shape within the temperature probe lumen. Once extended out of the lumen through the ramp, it assumes its substantially J-shape.

It will be appreciated that a J-shaped wire that is round may be rotated, and the distal tip of the probe may not be directed out away from the catheter. In order to assure proper orientation of the J tip away from the catheter, slot 30 is preferably in the form of a flat slot. The portion of temperature probe 20 that mates against this flat surface when the probe is extended is preferably in the form of a substantially flat probe. Thus, when the flat portion of the temperature probe encounters the flat ramp, the shape of the ramp orients the probe to ensure that the substantially J-shape extends outward away from the catheter shaft.

Accordingly, the catheter is inserted into a subject's blood vessel with the temperature probe retracted and the thermistors on the end of the probe within the temperature lumen in an undeployed state. By extending the temperature probe forward, the thermistor tip is moved through the slot and the temperature is thus deployed into the subject's blood stream.

Since the catheter is within a blood vessel, tip 40 of the thermistor preferably comprises an atraumatic tip. This helps prevent puncturing of the blood vessel or irritating the endothelium of the vessel if the temperature control probe encounters the wall of the blood vessel.

Figure 3B:
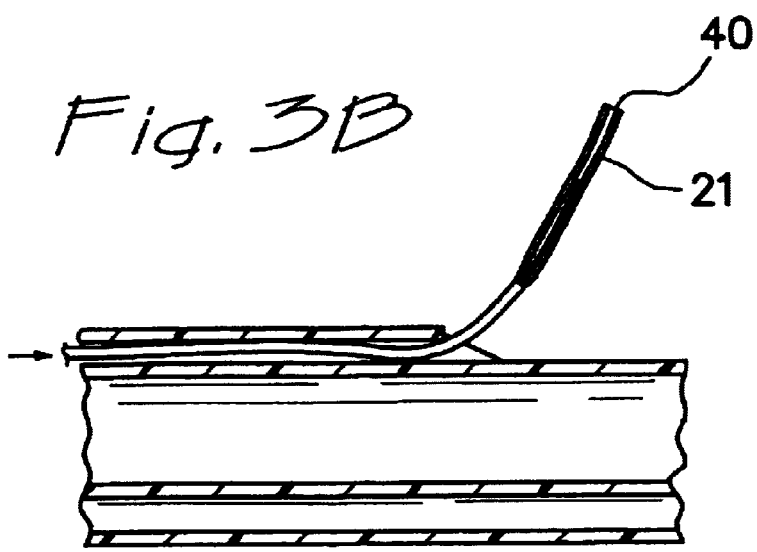
FIG. 3B is an sectional side view of a distal end portion of a temperature probe lumen in accordance with the present invention.

Other embodiments of an on-board temperature probe are clearly within the contemplation of this invention. With reference to FIG. 3A, it can be seen that instead of having a lumen within the catheter for a movable temperature probe as shown in FIG. 2A, a tube with a channel 50 may extend along the exterior of the catheter shaft. With the embodiment illustrated in FIG. 3A, the deployable temperature probe may be deployed into its substantially J-shape through a slot as illustrated in FIG. 3B.

Figure 5:
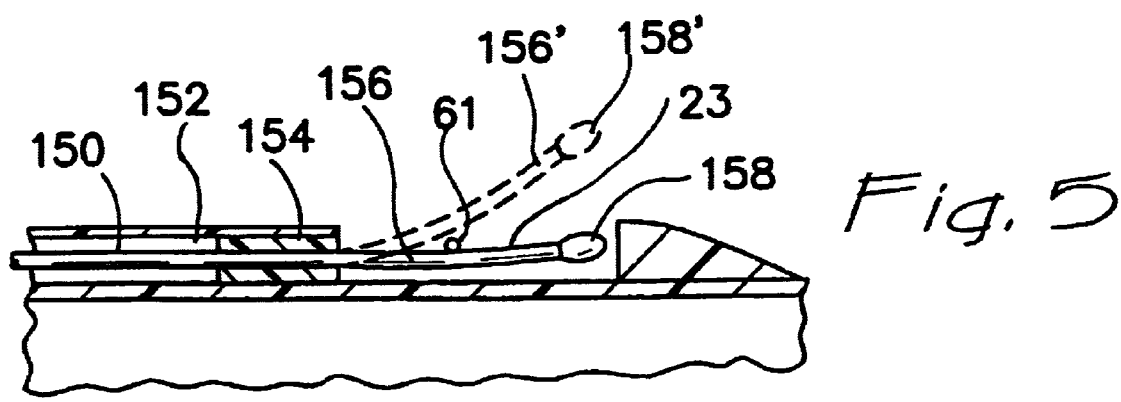
FIG. 5 is a sectional side view of a distal end portion of a temperature probe lumen in accordance with an alternative embodiment of the present invention.

FIG. 5 illustrates an alternative embodiment of the catheter system and the on-board temperature probe. The temperature probe 150 is fixedly contained within a temperature probe channel 152 and held in place by plug 154. The distal portion 156 of the temperature probe is upwardly biased so that if unrestrained it assumes a curved shape 156' with the tip extending outward away from the catheter body. A biodegradable band such as a suture 61 that may be rapidly dissolvable in blood restrains the distal portion against the shaft of the catheter. When the catheter is placed into the blood stream, the restraining band is dissolved and the distal portion of the probe assumes its curved configuration 156' with the temperature sensors in the tip 158' extending outward from the catheter shaft. Preferably this assumes a gentle J shape as described above to adequately locate the temperature sensor away from the catheter shaft but to have an atraumatic configuration. The distal portion of the probe may have a mechanical bias such as a fixed shape with spring-like bias, or it may have a temperature sensitive bias. That is, it may have a straight shape when at room temperature, but be made of a shape memory material such as Nitinol or various temperature memory plastics, so it is straight at room temperature but assumes a curved shape when it is warmed to body temperature by the blood. If this type of shape memory material is used, a restraining band need not be used, although it might also be used as an additional restraint. It should be noted that whenever a probe tip is described herein as biased in a particular configuration, that bias may be a permanent mechanical bias or it may be a bias that is temperature dependent as described herein, and both are within the contemplation of this invention.

FIG. 6 illustrates another embodiment wherein the temperature probe is fixed in its axial orientation, and uses a "pull wire" mechanism to deploy the distal portion of the temperature probe away from the catheter shaft. In this embodiment, two wires 70, 71 are used to deploy the temperature probe into the bloodstream. The distal portion is configured, either as a spring (not illustrated) or a solid portion with cut-out sections. The wires are attached to the tip at a location slightly off-center. By pulling on one wire or the other, the top of the distal portion is compressed, and the lower portion expands to deploy the temperature probe into the bloodstream, preferably in a gentle, substantially J-shape. Reversing the process may return the probe to its generally straight configuration and thus minimize its profile for insertion and withdrawal. Various mechanism for activating the pull wire or pull wires are known in the art and are not illustrated here.

Figure 8A:
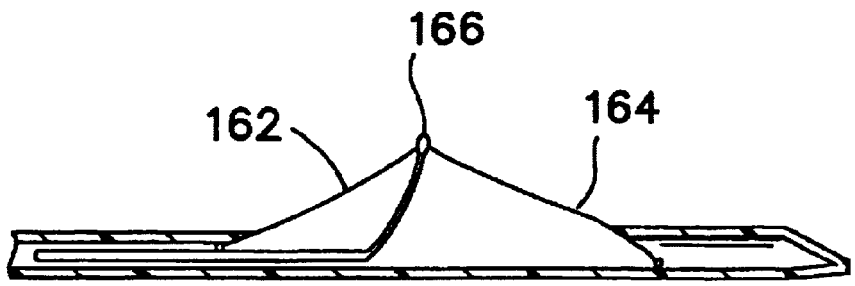
FIG. 8A is a sectional side view of a distal end portion of a catheter system of an alternative embodiment of the present invention with the probe shown in a deployed state.
Figure 8B:
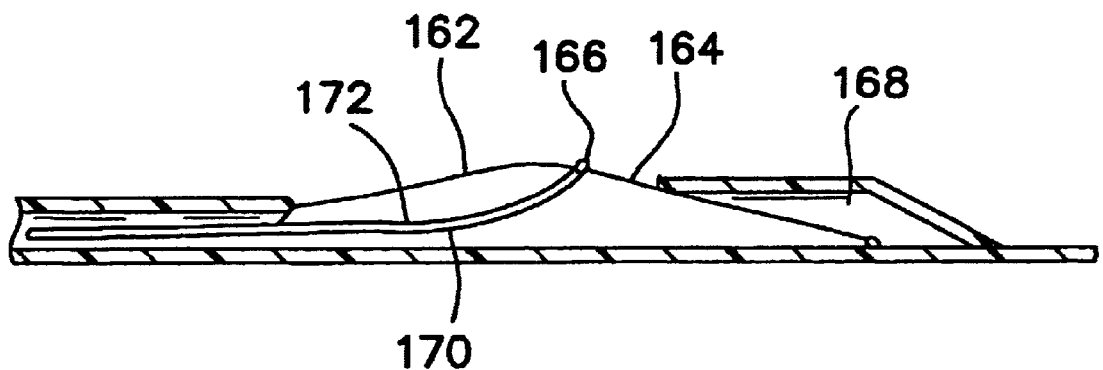
FIG. 8B is a sectional side view of a distal end portion of a temperature probe in accordance with an alternative embodiment of the present invention with the probe shown in a collapsed state.

Another embodiment of an on-board, deployable probe is illustrated in FIGS. 8A and 8B. An outwardly biased member comprised of two legs 162, 164 which may be a unitary member is provided at an appropriate location proximal of the heat exchange region. The temperature sensor, such as a thermistor 166 is located in the central portion between the two legs, so that when they assume their outward configuration (FIG. 8A) the temperature sensor is held outward away from the catheter shaft. In this embodiment, the legs may be rigid, for example a flat piece of plastic, and may be provided with a slot 168 in which to retract when compressed. In this Figure the slot is shown as provided for the forward leg, but it is equally acceptable for the forward leg to be fixed and the rear leg to retract when compressed. The upwardly biased member 162/164 may in fact be a curved member and not two distinct legs, as will be readily appreciated by those in the art. Alternatively, the upwardly biased member 162/164 may simply be compressible into a flat configuration and not a slidable configuration as illustrated.

The temperature sensor, such as thermistor 166, is attached to two signal carrying wires 170, 172 that carry the temperature sensing signal to the exterior plug 96. As stated previously, it is important that the wires be thermally insulated so that the temperature sensed by the thermistor 166 is that of the blood flowing over it and is not a temperature of the catheter shaft conducted up the wires 170, 172.

The deployed sensor of this embodiment has the advantage that nothing need be done to deploy the on-board sensor. That is, it is essentially always deployed, but will compress down against the shaft upon insertion through an introducer sheath so that it assumes a small profile for insertion, but will immediately spring back out when unconstrained in the bloodstream.

Figure 9A:
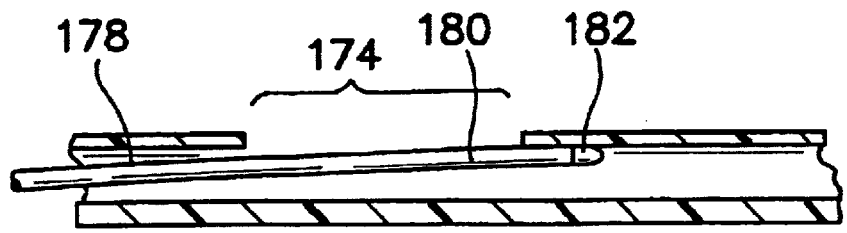
FIG. 9A is a sectional side view of a distal end portion of a temperature probe in accordance with an alternative embodiment of the present invention with the probe shown in an undeployed state.
Figure 9B:
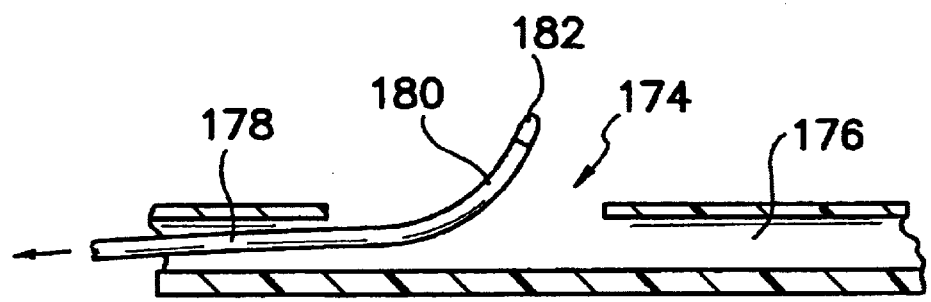
FIG. 9B is a sectional side view of a distal end portion of a temperature probe in accordance with an alternative embodiment of the present invention with the probe shown in a deployed state.
Figure 10A:
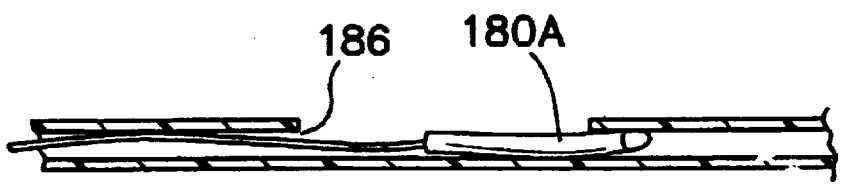
FIG. 10A is a sectional side view of a distal end portion of a temperature probe in accordance with an alternative embodiment of the present invention with the probe shown in an undeployed state.
Figure 10B:
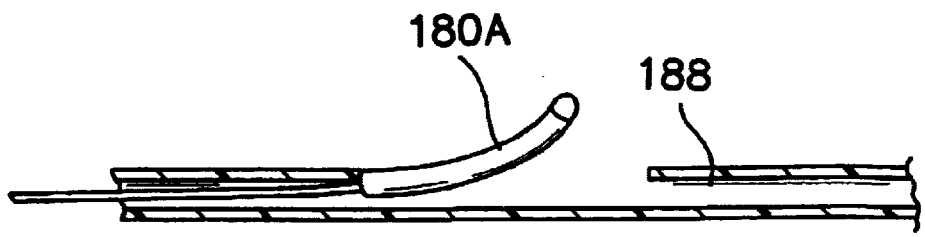
FIG. 10B is a sectional side view of a distal end portion of a temperature probe in accordance with an alternative embodiment of the present invention with the probe shown in a deployed state.

Yet another embodiment is depicted in FIGS. 9A and 9B. In this embodiment, a movable temperature probe 178 with an upwardly biased distal portion 180 is placed in a temperature probe lumen with an open window 174 and a closed distal end 176. Prior to being deployed the distal end of the probe is retained within the distal end 176 of the lumen. When the probe is withdrawn a short distance (shown in FIG. 9B) the upwardly biased portion exits through the window and assumes the curved configuration that orients the temperature sensor 182 away from the catheter shaft. When the catheter is subsequently withdrawn, the temperature probe will naturally fold down against the catheter shaft as it is being drawn through the introducer sheath.

Figure 18A:
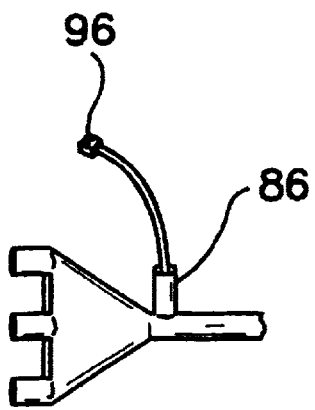
FIG. 18A is an elevational view of the proximal end of a catheter system of FIG. 17A where the with the distal end of the probe is undeployed.
Figure 18B:
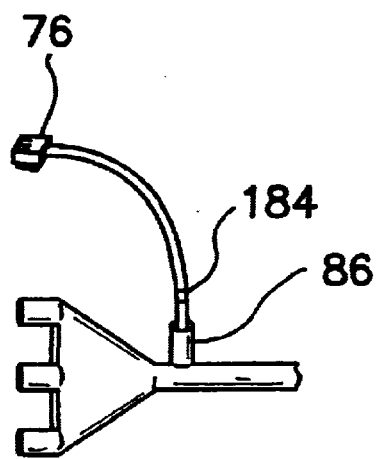
FIG. 18B is an elevational view of the proximal end of a catheter system of FIG. 17B with the distal end of the probe deployed.

Whenever the deployment of a temperature probe is accomplished by the axial movement of the probe, the amount of axial movement may be important in order to orient the temperature sensor the proper distance away from the catheter shaft. One method of doing so is shown in FIGS. 18A and 18B. An indicia, such as a marker band 184, may be located on the proximal end of the temperature probe, and when that marker is at the proper location that would indicate the amount of axial movement of the temperature probe. In the example illustrated, the probe is deployed by withdrawing the temperature probe, and the amount of withdrawal necessary is indicated when the marker band just clears the exit port 86. Of course, the same effect may be had if the marker band is used to indicate the advancement of the temperature probe as in FIG. 1; the marker would be placed farther up on the proximal end of the probe and the correct amount of advancement indicated when the marker band is at the correct location relative to the exit port 86. The probe may then be locked in place in any of various means; for example affixing a keyed or barbed channel with a mating shape on the probe surface.

Other means of ensuring the correct amount of axial movement may be seen in FIGS. 10A and 10B and 17A and 17B. In 10A a temperature probe with a large distal portion 180A is located in a temperature probe channel as in FIG. 9A. The proximal end of the large distal portion 180A of the temperature probe is too large in diameter to fit within the proximal portion 186 of the temperature probe channel and therefore when the temperature probe is withdrawn, it will only withdraw until the probe is withdrawn a certain distance. The probe distal portion 180A then assumes its J shape, either because of its permanent bias or temperature based memory shape.

Figure 17A:
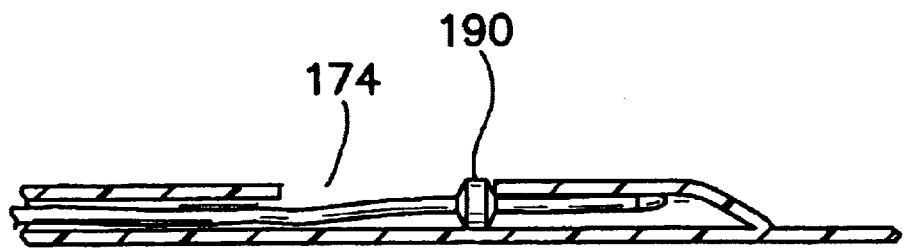
FIG. 17A is a sectional side view of a distal end portion of a temperature probe in accordance with an alternative embodiment of the present invention with the probe shown in an undeployed state.
Figure 17B:
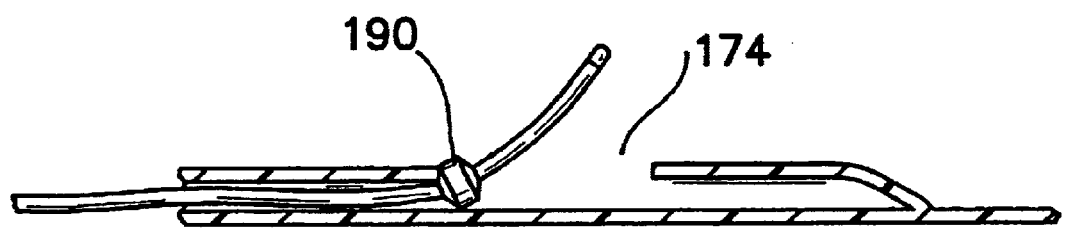
FIG. 17B is a sectional side view of a distal end portion of a temperature probe in accordance with an alternative embodiment of the present invention with the probe shown in a deployed state.

In this embodiment, the distal portion 188 of the channel must be large enough to accept the distal portion 180A of the probe, yet the proximal portion 186 of the channel must be small enough not to accept the proximal end of that portion of the temperature probe. If the proximal portion of the probe tip is tapered or otherwise of increased diameter, a channel of the same diameter could be used for both sections which has obvious manufacturing advantages. Another way in which this could be accomplished as shown in FIGS. 17A and 17B. In this example, a section of enlarged diameter 190 is contained on the temperature probe in the section located in the window 174. When the probe is withdrawn, it can only be withdrawn until the enlarged section contacts the proximal edge of the window. In this way the exact amount of axial movement of the probe can be predetermined, and the exact shape of the distal portion determined for placement of the temperature sensor the appropriate distance from the catheter shaft.

Figure 16A:
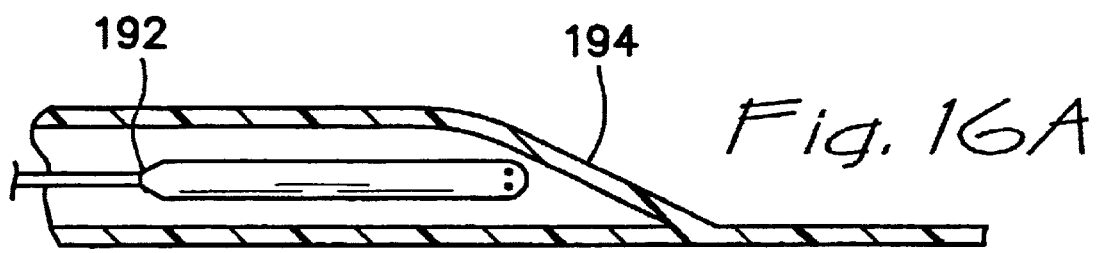
FIG. 16A is a sectional side view of a distal end portion of a temperature probe in accordance with an alternative embodiment of the present invention with the probe shown in an unadvanced state.
Figure 16B:
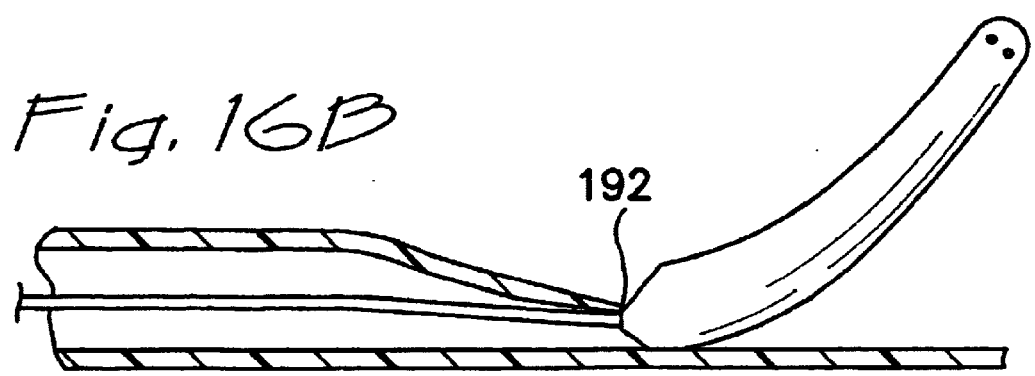
FIG. 16B is a sectional side view of a distal end portion of a temperature probe in accordance with an alternative embodiment of the present invention with the probe shown in an advanced state.

Another embodiment for accomplishing this precise amount of axial movement is shown in FIGS. 16A and 16B. In this embodiment, the probe has a location of sharp increase in diameter 192, and the distal end of the temperature probe lumen has a flap 194 that is biased down against the catheter shaft. When the temperature probe is advanced it can exit under the flap 194, but when it is withdrawn, it cannot be withdrawn past the location of increased diameter. In this way the probe may be deployed forward, and then pulled back to the correct, predetermined position and no farther.

These methods of determining position of the probe after deployment may, of course, be used alone or in combination with each other.

Figure 13A:
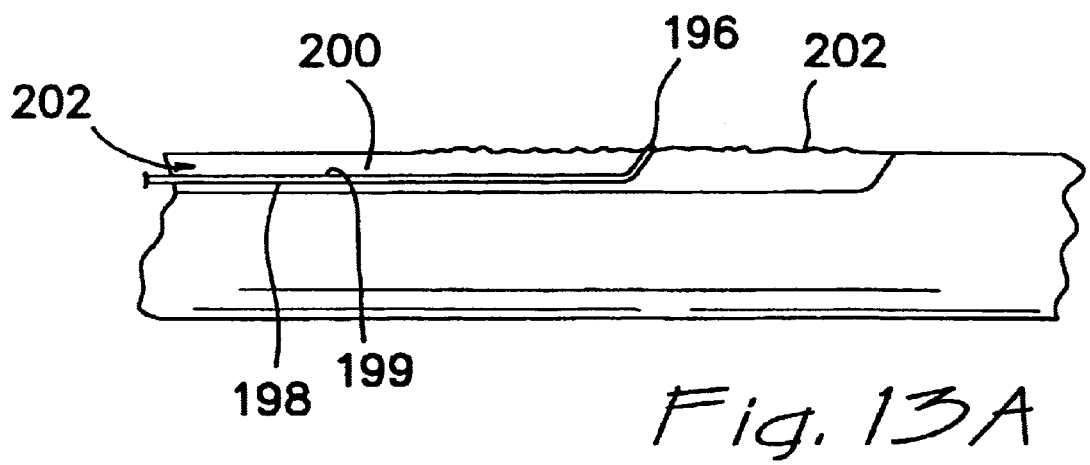
FIG. 13A is a sectional side view of a distal end portion of a temperature probe in accordance with an alternative embodiment of the present invention with the probe shown in an undeployed state.
Figure 13B:
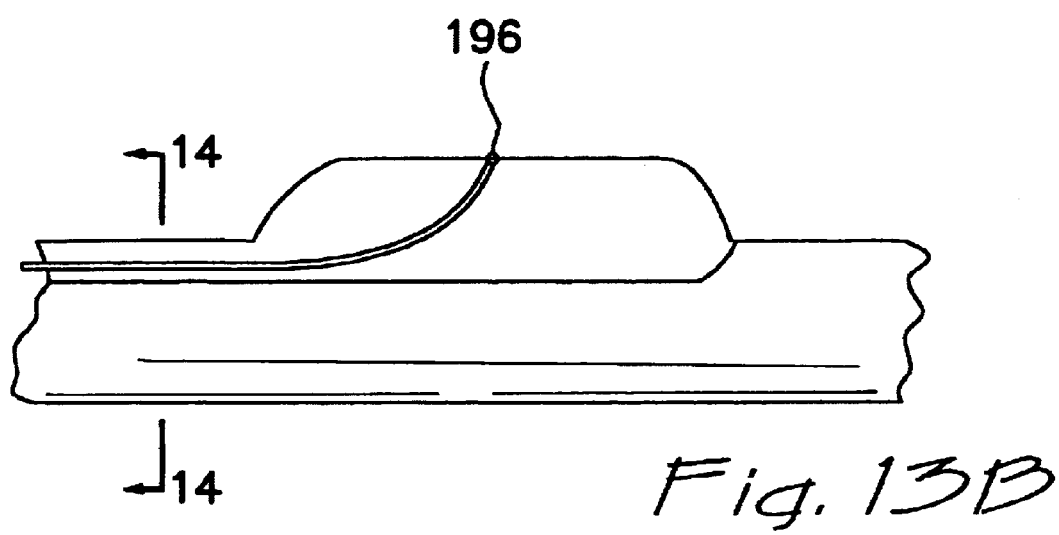
FIG. 13B is a sectional side view of a distal end portion of a temperature probe in accordance with an alternative embodiment of the present invention with the probe shown in a deployed state.
Figure 14:
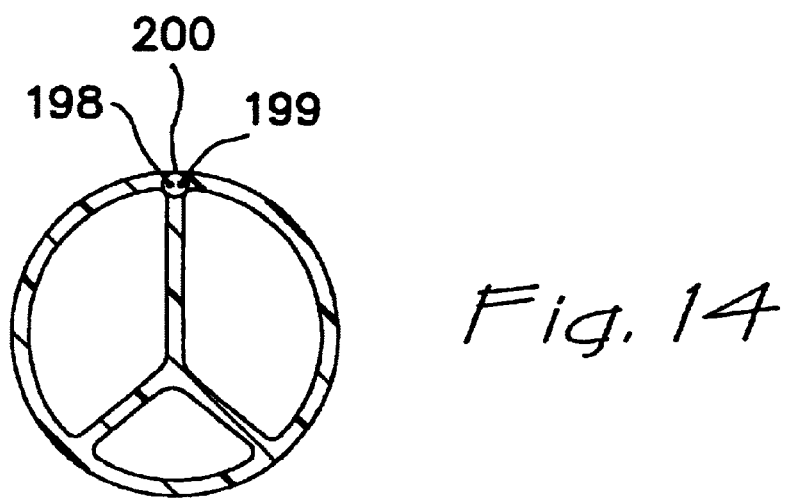
FIG. 14 is a cross section of the catheter system of the invention taken along the line 14—14 in FIG. 13B.

Another embodiment of an on-board temperature sensor that has one diameter, for insertion for example, and another diameter where the temperature sensor is held away from the catheter shaft is depicted in FIGS. 13A, 13B and 14. In this embodiment, the temperature sensor 196, such as a thermistor is located on a balloon 202. Insulated wires 198, 199 conduct temperature signals from the thermistor outside the patient's body to a controller. An inflation channel 200 permits the introduction of inflation medium for example saline or $CO_2$ to inflate the balloon. The balloon may be, for example, a non-compliant PET balloon that has a predetermined shape and size. When fully inflated, this holds the temperature sensor a predetermined distance out into the bloodstream. This has the advantage of permitting some insulation, for example the use of an insulating inflation medium such as $CO_2$ and providing a very atraumatic means of locating the temperature sensor away from the catheter. The presence of the balloon just upstream of the heat exchange region may have an additional benefit of causing mixing eddies in the fluid stream (blood stream) that may further enhance heat exchange between the heat exchange region and the blood.

Figure 15A:
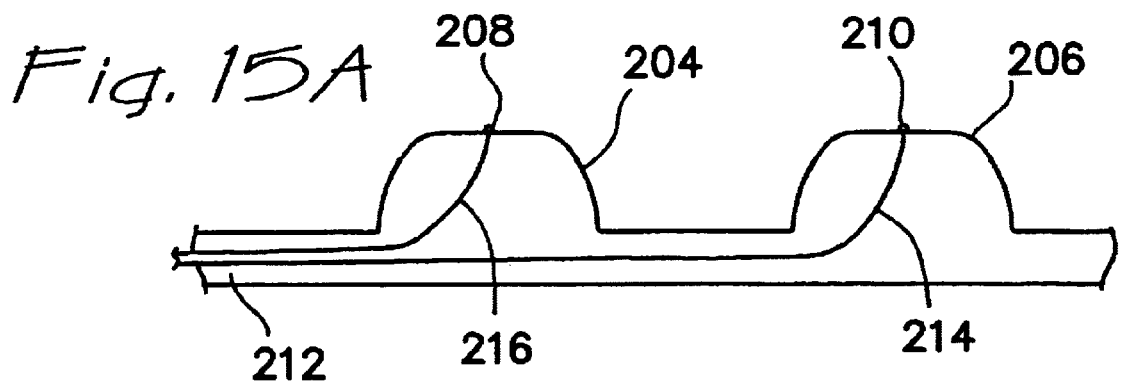
FIG. 15A a sectional side view of a distal end portion of a catheter system of the present invention.
Figure 15B:
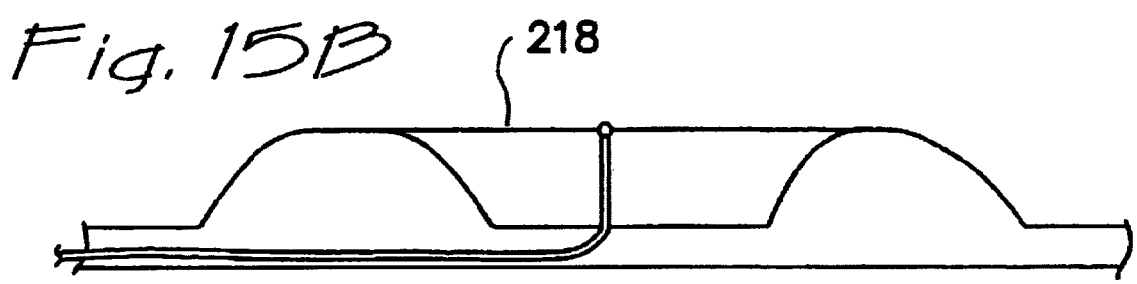
FIG. 15B is a sectional side view of a distal end portion of a catheter system in accordance with an alternative embodiment of the present invention.

Two balloons may be provided as shown in FIGS. 15A and 15B. In FIG. 15A each balloon 204, 206 is provided with a temperature sensor 208, 210. This may provide safety through redundancy or may provide for temperature measures at different locations. The two balloons may be located a different locations along a common lumen 212 and therefore the probe connecting wires 214, 216 for carrying the temperature signal may be located in the common lumen, and likewise the same lumen may serve as the inflation lumen for both balloons. Alternatively they may be independently controlled through independent inflation lumens.

In 15B, a temperature probe may be located on a wire, string, or other member 218 suspended between two balloons. This has the advantage of allowing the access to the temperature sensor from outside the catheter. In this situation it might be desirable to have the wires from the sensor travel outside the body through an external channel or not encased in a channel at all rather than locate them in the inflation channel.

Figure 11A:
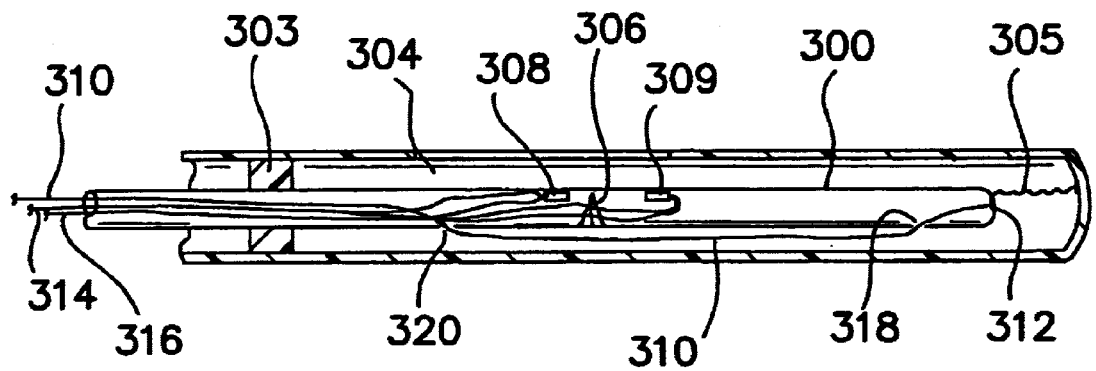
FIG. 11A is a sectional side view of a distal portion of a temperature probe in accordance with an alternative embodiment of the present invention with the probe shown in an undeployed state.
Figure 11B:
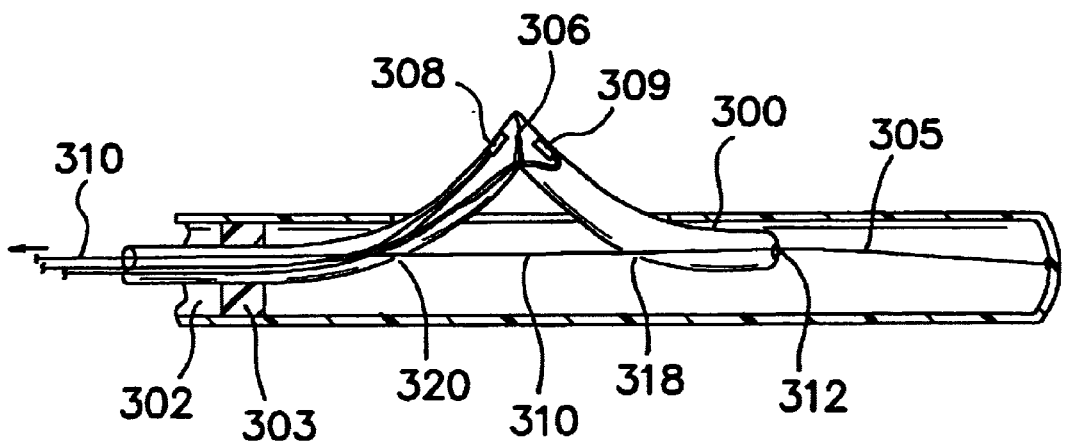
FIG. 11B is a sectional side view of a distal portion of a temperature probe in accordance with an alternative embodiment of the present invention with the probe shown in a deployed state.

Another embodiment is shown in FIGS. 11A and 11B. In this embodiment, a temperature probe 300 is in the form of a polyimide tube. The polyimide tube is contained in a temperature probe lumen 302. The lumen has a window 304 located at a location along the catheter, for example about 3 cm proximal to a heat exchange balloon. The probe is fixed in the probe lumen proximal of the window by, for example, adhesive 303.

At the location of the windows the polyimide tube is crimped 306. Near the location just proximal of the crimp, a thermistor 308 is located in or on the tube. A second thermistor 309 may be located just distal if the crimp to provide redundancy. Connector wires 314, 316 run from the thermisters to the plug the proximal end of the tube outside the patient's body.

The probe tube has two openings 318, 320 one on each side of the crimp. A pull wire 310 is affixed at the distal end 312 of the tube, and runs from that point of attachment inside the probe tube, out of the first opening 318, along the side of the probe tube, back into the tube through the second opening 320, and from there runs the length of the tube and is accessible to the operator at the proximal end (not shown).

In this embodiment, when undeployed, the temperature probe lies flat with sensors 308, 309 within the outer profile of the catheter and thus is insertable within any size introducer sheath that will suffice for the catheter. Once located in the desired location in the vasculature, the operator pulls the pull wire 310 which slides the distal portion of the probe tube backwards and causes the tube to bend at the crimp 306 and depoly the sensor through the window up and away from the catheter.

When the catheter is to be withdrawn, the pull wire may be pushed forward to once again cause the probe to lie flat in the probe lumen 302. In addition, the force of pulling the catheter back through the sheath can push in the deployed portion of the probe back down through the window and essentially return it to the undeployed position. Alternatively, or in addition, a biasing member such as a spring or elastomeric string 305 may attach the distal end of the tube 300 to a distal location in the probe lumen 302 so that the probe tube is pulled straight with the crimped portion within the window section of the tube unless the pull wire is withdrawn.

In this configuration, at the proximal end, a method of affixing the pull wire in the "pulled" configuration in a manner commonly known in the art, will allow the wire to be retracted, affixed in the retracted position which will fix the sensor in the deployed position. As discussed previously, methods of affixing the pull wire at a specific axial location will assure the proper amount of bending at the crimped location for proper deployment of the probe.

When the catheter is to be withdrawn, various devices for releasing the pull wire allow the catheter to be withdrawn with the probe in the undeployed configuration.

Figure 12A:
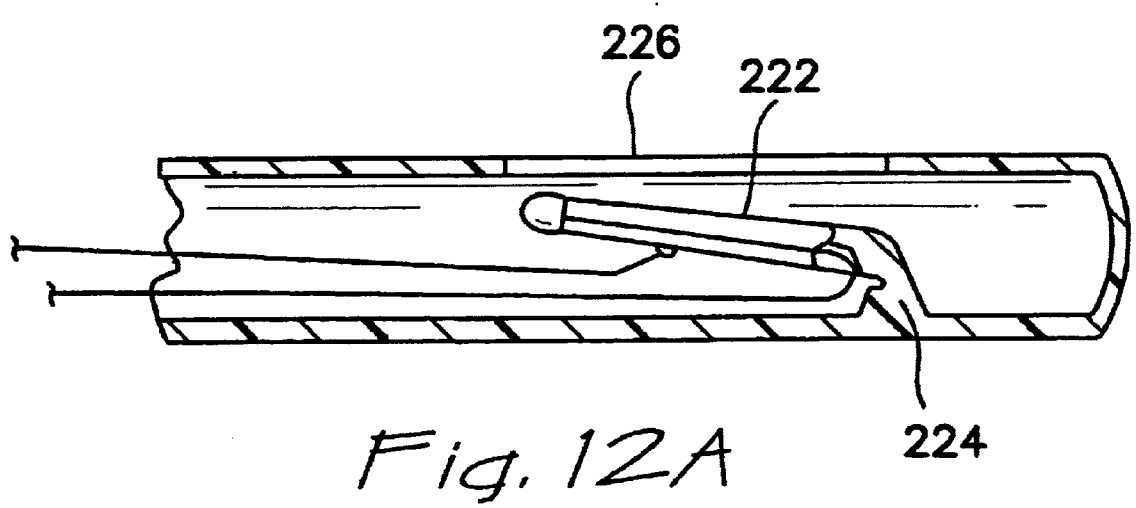
FIG. 12A is a sectional side view of a distal end portion of a temperature probe in accordance with an alternative embodiment of the present invention with the probe shown in an undeployed state.
Figure 12B:
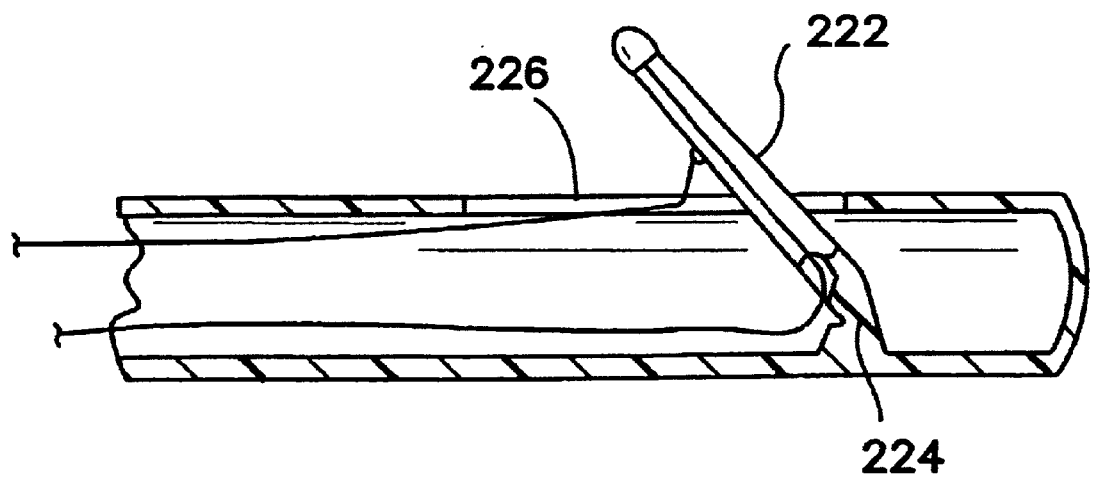
FIG. 12B is a sectional side view of a distal end portion of a temperature probe in accordance with an alternative embodiment of the present invention with the probe shown in a deployed state.

Similarly in FIGS. 12A and 12B an arm 222 hinged at an attachment to the catheter 224 may be raised away from the catheter body with a push wire, or relaxing of a restraining wire if the hinged arm has an upward bias.

Those skilled in the art will understand that other mechanisms and/or arrangements may be used to deploy the temperature probe into the bloodstream.

Although the present invention has been described with reference to specific exemplary embodiments, it will be appreciated that it is intended to cover all modifications and equivalents within the scope of the appended claims.

What is claimed is:

1. A catheter system for sensing the temperature of a patient, the catheter system comprising:
   a fluid flow heat exchange catheter having a shaft and a heat exchange region controlled by a flow of heat exchange fluid;
   a temperature probe lumen, the lumen defining an aperture that is located proximal of the heat exchange region;
   a deployable temperature probe, the temperature probe including a temperature sensor and a signal carrying mechanism that extends from the temperature sensor to a location outside of the patient, the temperature probe having an undeployed configuration and a deployed configuration, the temperature probe being movable between the undeployed and deployed configurations; and
   a removable constraint that constraints the amount of movement of the temperature probe within the temperature probe humen, the temperature probe moving to the deployed configuration upon removal of the constraint by an operator;
   wherein when the temperature probe is in the deployed configuration, the temperature sensor is located further from the shaft than when the temperature probe is in the undeployed configuration; and
   wherein the temperature sensor generates a signal representing a sensed temperature and the signal carrying mechanism transmits the signal from the temperature sensor to the location outside the patient.

2. A catheter system in accordance with claim 1 wherein the temperature sensor comprises a thermistor.

3. A catheter in accordance with claim 2 wherein the temperature sensor comprises a second thermistor.

4. A catheter system in accordance with claim 1 wherein the shaft includes fluid flow lumens for flow of heat exchange fluid to the heat exchange region.

5. A catheter system in accordance with claim 1 wherein the temperature probe is deployed to the deployed configuration by at least one pull wire.

6. A catheter system in accordance with claim 1 wherein the temperature probe is in the form of a tube containing thermistor wires.

7. A catheter system in accordance with claim 1 wherein the temperature probe lumen is within the catheter shaft and coupled thereto.

8. A catheter system in accordance with claim 1 wherein the temperature probe lumen is external to the catheter shaft and coupled thereto.

9. A catheter system in accordance with claim 8 wherein the temperature probe lumen extends along only a portion of the catheter shaft.

10. A catheter system in accordance with claim 8 wherein the temperature probe lumen extends along an entire length of an inserted portion of the catheter shaft.

11. A catheter system in accordance with claim 1 wherein the temperature probe lumen is incorporated within the catheter shaft and wherein the temperature probe lumen is extruded with the catheter shaft and is within the outer diameter of the shaft.

12. A catheter system in accordance with claim 1 wherein the aperture is located at a distal end of the temperature probe lumen.

13. A catheter system in accordance with claim 12 wherein the aperture comprises a ramp.

14. A catheter system in accordance with claim 13 wherein the ramp includes a shaped surface and the temperature probe includes a portion configured to mate with the shaped surface of the ramp.

15. A catheter system in accordance with claim 14 wherein the shaped surface is flat.

16. A catheter system in accordance with claim 1 wherein the temperature sensor is in a range of 1.8–3.2 mm from the catheter shaft when the temperature probe is in the deployed configuration and is within the outer diameter of the catheter shaft when the temperature probe is in the undeployed configuration.

17. A catheter system in accordance with claim 1 further comprising a controller for receiving the signals from the signal carrying mechanism, the controller being configured to use the signals to control the body temperature of the patient by modifying the temperature of blood flowing within a blood vessel of the patient.

18. A catheter system in accordance with claim 1 wherein the catheter includes an atraumatic tip.

19. A method of monitoring the body temperature of a patient by monitoring the temperature of blood flowing within a blood vessel of the patient, the method comprising:
   advancing a catheter body comprising a temperature probe lumen that extends along a catheter shaft and that includes an opening defined at a distal end portion into the patient's blood vessel such that the opening is in contact with the patient's blood; and
   deploying a temperature probe from within the temperature probe lumen such that a distal end portion of the temperature probe protrudes through the opening into the blood flowing within the blood vessel, wherein the deployable temperature probe comprises shape memory material at a tip portion at the distal end portion such that when it warms, it curves through the opening.

20. A method in accordance with claim 19 wherein the distal end of the temperature probe lumen includes a ramp coupled to the opening thereby guiding the distal end portion through the opening.

21. A method in accordance with claim 19 wherein the temperature sensed is venous blood.

22. A method in accordance with claim 20 wherein the blood vessel is the inferior vena cava.

23. A method in accordance with claim 20 wherein the blood vessel is the femoral vein.

24. A catheter system for sensing the temperature of a patient, the catheter system comprising:
   a catheter having a shaft and a heat exchange region;
   a temperature probe lumen, the lumen defining an aperture that is located proximal of the heat exchange region; and
   a deployable temperature probe, the temperature probe including a temperature sensor, a signal carrying mechanism that extends from the temperature sensor to a location outside of the patient, and a constraint that constrains the amount of movement of the temperature probe within the temperature probe lumen, the temperature probe having an undeployed configuration and a deployed configuration, the temperature probe being movable from the undeployed configuration to the deployed configuration upon removal of the constraint by an operator;

wherein when the temperature probe is in the deployed configuration, the temperature sensor is located further from the shaft than when the temperature probe is in the undeployed configuration; and wherein the temperature sensor generates a signal representing a sensed temperature and the signal carrying mechanism transmits the signal from the temperature sensor to the location outside the patient.

25. A catheter system for sensing the temperature of a patient, the catheter system comprising:

a catheter having a shaft and a heat exchange region;

a temperature probe lumen, the lumen defining an aperture that is located proximal of the heat exchange region; and a deployable temperature probe, the temperature probe including a temperature sensor and a signal carrying mechanism that extends from the temperature sensor to a location outside of the patient, the temperature probe having an undeployed configuration and a deployed configuration, the temperature probe being heat activated to move automatically between the undeployed and deployed configurations;

wherein when the temperature probe is in the deployed configuration, the temperature sensor is located further from the shaft than when the temperature probe is in the undeployed configuration; and wherein the temperature sensor generates a signal representing a sensed temperature and the signal carrying mechanism transmits the signal from the temperature sensor to the location outside the patient.

26. A catheter system in accordance with claim 25 wherein the temperature probe comprises nitinol.

27. A catheter system for sensing the temperature of a patient, the catheter system comprising:

a catheter having a shaft and a heat exchange region;

a temperature probe lumen, the lumen defining an aperture that is located proximal of the heat exchange region; and a deployable temperature probe, the temperature probe including a temperature sensor and a signal carrying mechanism that extends from the temperature sensor to a location outside of the patient, the temperature probe having an undeployed configuration and a deployed configuration, the temperature probe being spring activated to move automatically between the undeployed and deployed configurations;

wherein when the temperature probe is in the deployed configuration, the temperature sensor is located further from the shaft than when the temperature probe is in the undeployed configuration; and wherein the temperature sensor generates a signal representing a sensed temperature and the signal carrying mechanism transmits the signal from the temperature sensor to the location outside the patient.

28. A catheter system for sensing the temperature of a patient, the catheter system comprising:

a catheter having a shaft and a heat exchange region;

a temperature probe lumen, the lumen defining an aperture that is located proximal of the heat exchange region; and a deployable temperature probe, the temperature probe including a temperature sensor, a signal carrying mechanism that extends from the sensor to a location outside of the patient, and a biodegradable restraining element the temperature probe having an undeployed configuration and a deployed configuration, the temperature probe being automatically movable between the undeployed and deployed configurations;

wherein when the temperature probe is in the deployed configuration, the temperature sensor is located further from the shaft than when the temperature probe is in the undeployed configuration; and wherein the temperature sensor generates a signal representing a sensed temperature and the signal carrying mechanism transmits the signal from the temperature sensor to the location outside the patient.

29. A catheter system for sensing the temperature of a patient, the catheter system comprising:

a catheter having a shaft and a heat exchange region;

a temperature probe lumen, the lumen defining an aperture that is located proximal of the heat exchange region; and a deployable temperature probe, the temperature probe including a temperature sensor and a signal carrying mechanism that extends from the sensor to a location outside of the patient, the temperature probe having an undeployed configuration and a deployed configuration, the temperature probe being movable between the undeployed and deployed configurations;

a controller for receiving signals from the signal carrying mechanism, the controller being configured to use the signals to control the body temperature of the patient by modifying the temperature of blood flowing within a blood vessel of the patient;

wherein when the temperature probe is in the deployed configuration, the temperature sensor is located further from the shaft than when the temperature probe is in the undeployed configuration; and wherein the temperature sensor generates a signal representing a sensed temperature and the signal carrying mechanism transmits the signal from the temperature sensor to the location outside the patient.

30. A method of monitoring the body temperature of a patient by monitoring the temperature of blood flowing within a blood vessel of the patient, the method comprising:

inserting a catheter body into the patient's blood vessel, the catheter body including a temperature probe lumen that extends along a catheter shaft, the temperature probe lumen including an opening defined at a distal end portion of the lumen and a ramp coupled to the opening;

advancing the catheter body such that the opening is in contact with the patient's blood; and deploying a temperature probe from within the temperature probe lumen such that the ramp guides a distal end portion of the temperature probe through the opening and into the blood flowing within the blood vessel;

wherein the blood vessel is selected from the group consisting of the inferior vena cava and the femoral artery.

31. A method in accordance with claim 30 wherein the blood vessel is the inferior vena cava.

32. A method in accordance with claim 30 wherein the blood vessel is the femoral vein.

33. A catheter system for sensing the temperature of a patient, the catheter system comprising:

a fluid flow heat exchange catheter having a shaft and a heat exchange region controlled by a flow of heat exchange fluid;

a temperature probe lumen, the lumen defining an aperture that is located proximal of the heat exchange region; and a deployable temperature probe selected from the group consisting of
- a heat-activated temperature probe,
- a spring-activated temperature probe, and
- a temperature probe having a biodegradable restraining element, the temperature probe including a temperature sensor and a signal carrying mechanism that extends from the temperature sensor to a location outside of the patient, the temperature probe having an undeployed configuration and a deployed configuration, the temperature probe being automatically movable between the undeployed and deployed configurations;

wherein when the temperature probe is in the deployed configuration, the temperature sensor is located further from the shaft than when the temperature probe is in the undeployed configuration; and wherein the temperature sensor generates a signal representing a sensed temperature and the signal carrying mechanism transmits the signal from the temperature sensor to the location outside the patient.

34. A catheter system in accordance with claim 33 wherein the temperature probe is heat activated.

35. A catheter system in accordance with claim 34 wherein the temperature probe comprises a shape-memory material.

36. A catheter system in accordance with claim 35 wherein the temperature probe comprises nitinol.

37. A catheter system in accordance with claim 33 wherein the temperature probe is spring activated.

38. A catheter system in accordance with claim 33 wherein the temperature probe includes a biodegradable restraining element.

* * * * *